United States Patent [19]
Iwaki et al.

[11] Patent Number: 5,827,691
[45] Date of Patent: Oct. 27, 1998

[54] PROCESS FOR PREPARING A PROTEIN WHICH INHIBITS METASTASIS OF CANCER

[75] Inventors: Kanso Iwaki; Tsunetaka Ohta; Masashi Kurimoto, all of Okayama, Japan

[73] Assignee: Kabushiki Kaisha Hayashibara Seibutsu Kagaku Kenkyujo, Okayama, Japan

[21] Appl. No.: 827,864

[22] Filed: Apr. 9, 1997

Related U.S. Application Data

[60] Continuation of Ser. No. 555,857, Nov. 13, 1995, abandoned, which is a division of Ser. No. 127,278, Sep. 27, 1993, Pat. No. 5,498,697.

[30] Foreign Application Priority Data

Sep. 28, 1992 [JP] Japan .................................. 4-281136

[51] Int. Cl.[6] ............................. C12P 21/02; C07K 14/47
[52] U.S. Cl. .................... 435/69.1; 530/412; 530/416; 530/418; 530/422; 530/427; 530/350
[58] Field of Search ..................... 530/412, 416, 530/418, 422, 427, 350; 435/69.1

[56] References Cited

U.S. PATENT DOCUMENTS 5,126,148 6/1992 Kurimoto et al. ...................... 424/577

FOREIGN PATENT DOCUMENTS 0149751 7/1985 European Pat. Off. .
0401997 12/1990 European Pat. Off. .
2125048 2/1984 United Kingdom .

OTHER PUBLICATIONS

Jakob et al, Molecular Cloning and Sequence Analysis of DNA's . . . Aminoacylase, Biological Chemistry, vol. 372, p. 684, 1991.

Cook et al, Cloning, Sequence and Expression Analysis of a Chromosome . . . Cancer, J. Biol. Chem. vol. 268, pp. 17010–17017, 1993.

Y.E. Miller et al, Human Aminoacylase–1: Cloning, Regional Assignment . . . Chromosome 18, Genomics, vol. 8, pp. 149–154, 1990.

Y. Naomoto et al, Journal of Cancer Research and Clinical Oncology, vol. 113, 1987, pp. 544–549.

U.K. Laemmli, Nature, vol. 227, 1970, pp. 680–685.

J. Sambrook et al, Molecular Cloning: A Laboratory Manual, Cold Spring Harbor Laboratory Press, 1989, Chapter 8, "Construction and Analysis of cDNA Laboratories", pp. 8.2–8.6.

*Primary Examiner*—Charles L. Patterson, Jr.
*Assistant Examiner*—Gabriele E. Bugaisky
*Attorney, Agent, or Firm*—Browdy and Neimark

[57] ABSTRACT

Disclosed is a novel protein which has a molecular weight of 45,000±5,000 and pI 5.7±0.5 and exhibits cancer metastasis-inhibitory activity. The protein can be prepared by culturing human cells, animal cells and microorganisms capable of producing the protein in a nutrient culture medium while stimulating them with an inducer such as *Bacille Calmette-Guérin* and lipopolysaccharide.

5 Claims, No Drawings

PROCESS FOR PREPARING A PROTEIN WHICH INHIBITS METASTASIS OF CANCER

This application is a continuation, of application Ser. No. 08/555,857, filed Nov. 13, 1995, now abandoned is a division of parent application Ser. No. 08/127,278 filed Sep. 27, 1993, now U.S. Pat. No. 5,498,697.

BACKGROUND OF THE INVENTION

1. Field of the Invention

The present invention relates to a novel protein, and a DNA coding said protein, as well as to the preparation of said protein.

2. Description of the Prior Art

Nowadays, the treatment of cancers is mainly by surgical operations, chemotherapies and radiotherapies. Although most cancers may be cured by such a treatment, some viable cancer cells remaining after such a treatment may be, scattered throughout the body of a cancer patient, and may cause a more serious cancer-metastasis and even shorten the patient's life span. If the metastasis of cancers can be inhibited, cancer patients's pain would be relieved, and their life spans would be extended much more. Therefore, the development of agents which effectively inhibit the metastasis of cancers has been in great demand. In general, the metastasis of cancers, however, has been considered to occur via a complicated process, and this hinders the realization of satisfiable cancer metastasis-inhibitory agents.

Although a variety of proteins possessing cancer metastasis-inhibitory activity have been reported, the present protein absolutely differs from them. Examples of such a conventional protein are interferons and interleukin 2 which have been reported to have cancer metastasis-inhibitory activity. The present protein clearly differs from such a conventional protein in molecular weight and amino acid sequence. No conventional proteins have yet been realized as a cancer metastasis-inhibitory agent. In Japanese Patent Laid-Open No.308,799/90, a cancer metastasis-inhibitory factor produced by cells derived from human hematopoietic tissues is reported and its structure and physicochemical properties are, however, far from substantial elucidation because the description in the patent is vague and it only teaches the molecular weight ranging 10,000–450,000.

OBJECTS OF THE INVENTION

One object of the present invention is to provide a novel protein which effectively inhibits the metastasis of cancers.

Another object of the invention is to provide a DNA coding said protein.

Further object of the invention is to provide the preparation of said protein.

SUMMARY OF THE INVENTION

In order to attain the aforesaid objects, the present inventors studied substances which inhibit the metastasis of cancers. The present inventors continued studies in order to obtain a novel cancer metastasis-inhibitory substance, and, as a result eventually found cancer metastasis-inhibitory activity in a culture supernatant of HPB-MLT cell (FERM BP-2430), an established cell line derived from human T-cell leukemia, which had been stimulated in a nutrient culture medium with BCG and LPS. The present inventors revealed that the entity of the activity is a protein having the following physicochemical properties:

(1) Molecular weight 45,000±5,000;

(2) Isoelectric point pI=5.7±0.5;

(3) Partial amino acid sequence Possessing a partial amino acid sequence of Asp-Ser-Glu-Gly-Tyr-Ile-Tyr-Ala-Arg-Gly-Ala-Gln-Asp-Met-Lys (SEQ ID NO:1) or Glu-His-Trp-Ser-His-Asp-Pro-Phe-Glu (SEQ ID NO: 2);

(4) Solubility in solvent Soluble in water, physiological saline and phosphate buffer;

(5) Biological activity Exhibiting a metastasis-inhibitory activity on RPMI 4788 cell (FERM BP-2429), an established cell line derived from human colon cancer; and (6) Stability Inactivated in water at pH 7.2 and 100° C. for 30 minutes.

Stable in water at pH 7.2 and 4° C. for one month.

DETAILED DESCRIPTION OF THE INVENTION

The present inventors isolated a protein possessing cancer metastasis-inhibitory activity from a culture of HPB-MLT cell (FERM BP-2430) stimulated with BCG and LPS. The present inventors revealed the physicochemical properties of said protein and found that it has the amino acid sequence as shown in Chemical formula 1 (SEQ ID NO:4). The wording "substantially has the amino acid sequence as shown in Chemical formula 1" as referred to in the invention means that it should not be restricted to that as shown in Chemical formula 1 and shall include all the homologous variants thereof. In other words, the present invention includes any protein having a partial amino acid sequence in the amino acid sequence as shown in Chemical formula 1 as long as it possesses the same physicochemical properties as the above-mentioned protein.

Chemical formula 1 (SEQ ID no:4)

```
  1 Met—Thr—Ser—Lys—Gly—Pro—Glu—Glu—Glu—His—
 11 Pro—Ser—Val—Thr—Leu—Phe—Arg—Gln—Tyr—Leu—
 21 Arg—Ile—Arg—Thr—Val—Gln—Pro—Lys—Pro—Asp—
 31 Tyr—Gly—Ala—Ala—Val—Ala—Phe—Phe—Glu—Glu—
 41 Thr—Ala—Arg—Gln—Leu—Gly—Leu—Gly—Cys—Gln—
 51 Lys—Val—Glu—Val—Ala—Pro—Gly—Tyr—Val—Val—
 61 Thr—Val—Leu—Thr—Trp—Pro—Gly—Thr—Asn—Pro—
 71 Thr—Leu—Ser—Ser—Ile—Leu—Leu—Asn—Ser—His—
 81 Thr—Asp—Val—Val—Pro—Val—Phe—Lys—Glu—His—
 91 Trp—Ser—His—Asp—Pro—Phe—Glu—Ala—Phe—Lys—
101 Asp—Ser—Glu—Gly—Tyr—Ile—Tyr—Ala—Arg—Gly—
111 Ala—Gln—Asp—Met—Lys—Cys—Val—Ser—Ile—Gln—
121 Tyr—Leu—Glu—Ala—Val—Arg—Arg—Leu—Lys—Val—
131 Glu—Gly—His—Arg—Phe—Pro—Arg—Thr—Ile—His—
141 Met—Thr—Phe—Val—Pro—Asp—Glu—Glu—Val—Gly—
151 Gly—His—Gln—Gly—Met—Glu—Leu—Phe—Val—Gln—
161 Arg—Pro—Glu—Phe—His—Ala—Leu—Arg—Ala—Gly—
171 Phe—Ala—Leu—Asp—Glu—Gly—Ile—Ala—Asn—Pro—
181 Thr—Asp—Ala—Phe—Thr—Val—Phe—Tyr—Ser—Glu—
191 Arg—Ser—Pro—Trp—Trp—Val—Arg—Val—Thr—Ser—
201 Thr—Gly—Arg—Pro—Gly—His—Ala—Ser—Arg—Phe—
211 Met—Glu—Asp—Thr—Ala—Ala—Glu—Lys—Leu—His—
221 Lys—Val—Val—Asn—Ser—Ile—Leu—Ala—Phe—Arg—
231 Glu—Lys—Glu—Trp—Gln—Arg—Leu—Gln—Ser—Asn—
241 Pro—His—Leu—Lys—Glu—Gly—Ser—Val—Thr—Ser—
251 Val—Asn—Leu—Thr—Lys—Leu—Glu—Gly—Gly—Val—
261 Ala—Tyr—Asn—Val—Ile—Pro—Ala—Thr—Met—Ser—
271 Ala—Ser—Phe—Asp—Phe—Arg—Val—Ala—Pro—Asp—
281 Val—Asp—Phe—Lys—Ala—Phe—Glu—Glu—Gln—Leu—
291 Gln—Ser—Trp—Cys—Gln—Ala—Ala—Gly—Glu—Gly—
301 Val—Thr—Leu—Glu—Phe—Ala—Gln—Lys—Trp—Met—
```

-continued

Chemical formula 1 (SEQ ID no:4)

311 His—Pro—Gln—Val—Thr—Pro—Thr—Asp—Asp—Ser—
321 Asn—Pro—Trp—Trp—Ala—Ala—Phe—Ser—Arg—Val—
331 Cys—Lys—Asp—Met—Asn—Leu—Thr—Leu—Glu—Pro—
341 Glu—Ile—Met—Pro—Ala—Ala—Thr—Asp—Asn—Arg—
351 Tyr—Ile—Arg—Ala—Val—Gly—Val—Pro—Ala—Leu— sequences usable in the invention are, for example, those formed by a genetic code degeneracy wherein one or more bases in Chemical formula 2 are replaced with other bases, those which code the aforesaid homologous variants, and those which are complementary to the base sequence as shown in Chemical formula 2. The complementary base sequences may be wholly or partially complementary to that as shown in Chemical formula 2.

Chemical formula 2 (SEQ ID no:3)

| | | | | | | | | |
|---|---|---|---|---|---|---|---|---|
| 1 ATG | ACC | AGC | AAG | GGT | CCC | GAG | GAG GAG | CAC |
| 31 CCA | TCG | GTG | ACG | CTC | TTC | CGC | CAG TAC | CTG |
| 61 CGT | ATC | CGC | ACT | GTC | CAG | CCC | AAG CCT | GAC |
| 91 TAT | GGA | GCT | GCT | GTG | GCT | TTC | TTT GAG | GAG |
| 121 ACA | GCC | CGC | CAG | CTG | GGC | CTG | GGC TGT | CAG |
| 151 AAA | GTA | GAG | GTG | GCA | CCT | GGC | TAT GTG | GTG |
| 181 ACC | GTG | TTG | ACC | TGG | CCA | GGC | ACC AAC | CCT |
| 211 ACA | CTC | TCC | TCC | ATC | TTG | CTC | AAC TCC | CAC |
| 241 ACG | GAT | GTG | GTG | CCT | GTC | TTC | AAG GAA | CAT |
| 271 TGG | AGT | CAC | GAC | CCC | TTT | GAG | GCC TTC | AAG |
| 301 GAT | TCT | GAG | GGC | TAC | ATC | TAT | GCC AGG | GGT |
| 331 GCC | CAG | GAC | ATG | AAG | TGC | GTC | AGC ATC | CAG |
| 361 TAC | CTG | GAA | GCT | GTG | AGG | AGG | CTG AAG | GTG |
| 391 GAG | GGC | CAC | CGG | TTC | CCC | AGA | ACC ATC | CAC |
| 421 ATG | ACC | TTT | GTG | CCT | GAT | GAG | GAG GTT | GGG |
| 451 GGT | CAC | CAA | GGC | ATG | GAG | CTG | TTC GTG | CAG |
| 481 CGG | CCT | GAG | TTC | CAC | GCC | CTG | AGG GCA | GGC |
| 511 TTT | GCC | CTG | GAT | GAG | GGC | ATA | GCC AAT | CCC |
| 541 ACT | GAT | GCC | TTC | ACT | GTC | TTT | TAT AGT | GAG |
| 571 CGG | AGT | CCC | TGG | TGG | GTG | CGG | GTT ACC | AGC |
| 601 ACT | GGG | AGG | CCA | GGC | CAT | GCC | TCA CGC | TTC |
| 631 ATG | GAG | GAC | ACA | GCA | GCA | GAG | AAG CTG | CAC |
| 661 AAG | GTT | GTA | AAC | TCC | ATC | CTG | GCA TTC | CGG |
| 691 GAG | AAG | GAA | TGG | CAG | AGG | CTG | CAG TCA | AAC |
| 721 CCC | CAC | CTG | AAA | GAG | GGG | TCC | GTG ACC | TCC |
| 751 GTG | AAC | CTG | ACT | AAG | CTA | GAG | GGT GGC | GTG |
| 781 GCC | TAT | AAC | GTG | ATA | CCT | GCC | ACC ATG | AGC |
| 811 GCC | AGC | TTT | GAC | TTC | CGT | GTG | GCA CCG | GAT |
| 841 GTG | GAC | TTC | AAG | GCT | TTT | GAG | GAG CAG | CTG |
| 871 CAG | AGC | TGG | TGC | CAG | GCA | GCT | GGC GAG | GGG |
| 901 GTC | ACC | CTA | GAG | TTT | GCT | CAG | AAG TGG | ATG |
| 931 CAC | CCC | CAA | GTG | ACA | CCT | ACT | GAT GAC | TCA |
| 961 AAC | CCT | TGG | TGG | GCA | GCT | TTT | AGC CGG | GTC |
| 991 TGC | AAG | GAT | ATG | AAC | CTC | ACT | CTG GAG | CCT |
| 1021 GAG | ATC | ATG | CCT | GCT | GCC | ACT | GAC AAC | CGC |
| 1051 TAT | ATC | CGC | GCG | GTG | GGG | GTC | CCA GCT | CTA |
| 1081 GGC | TTC | TCA | CCC | ATG | AAC | CGC | ACA CCT | GTG |
| 1111 CTG | CTG | CAC | GAC | CAC | GAT | GAA | CGG CTG | CAT |
| 1141 GAG | GCT | GTG | TTC | CTC | CGT | GGG | GTG GAC | ATA |
| 1171 TAT | ACA | CGC | CTG | CTG | CCT | GCC | CTT GCC | AGT |
| 1201 GTG | CCT | GCC | CTG | CCC | AGT | GAC | AGC | |

-continued

Chemical formula 1 (SEQ ID no:4)

361 Gly—Phe—Ser—Pro—Met—Asn—Arg—Thr—Pro—Val—
371 Leu—Leu—His—Asp—His—Asp—Glu—Arg—Leu—His—
381 Glu—Ala—Val—Phe—Leu—Arg—Gly—Val—Asp—Ile—
391 Tyr—Thr—Arg—Leu—Leu—Pro—Ala—Leu—Ala—Ser—
401 Val—Pro—Ala—Leu—Pro—Ser—Asp—Ser

Based on the above-mentioned amino acid sequence, the present inventors screened DNAs which might code the present protein from HPB-MLT cell, and found that the present protein contained the base sequence as shown in Chemical formula 2 (SEQ ID NO:3). The DNA according to the present invention is not restricted to that as shown in Chemical formula 2. The wording "substantially has the base sequence as shown in Chemical formula 2" as referred to in the invention means that it has the whole or a part of the base sequence of Chemical formula 2. The base Furthermore, the present invention provides a process to prepare the above-mentioned protein, comprising culturing a cell capable of producing said protein in a nutrient culture medium to form said protein, and recovering the resultant protein from the culture. Examples of such a cell are established cell lines derived from human T-cell leukemia such as HPB-MLT cell and MOLT-4 cell (ATCC CRL 1582), and not restricted to those of human origin. Similarly as the cells of human origin, cells of animal origin and microorganisms can be advantageously used in the invention as long as they can inherently produce the present protein, and those into which had been introduced the present DNA by conventional cell fusion or genetic engineering technique can be advantageously used in the invention as long as the present protein is recovered from their cultures.

The cells usable in the present process are not restricted to those described in the present specification, and, if necessary the present protein can be prepared by culturing any one of the cells in a nutrient culture medium while stimulating it with an adequate stimulant such as BCC and LPS, and recovering the resultant protein having a metastasis-inhibitory activity from the resultant cells or supernatant. The cultivation of such a cell is carried out according to conventional techniques for animal cells and microorganisms. Conventional nutrient culture media containing vitamins, minerals, carbohydrates and the like can be employed in the invention. The recovering methods suitably used in the invention are two or more methods usually used in the purification of physiologically-active proteinous substances: For example, salting out, dialysis, centrifugation, gel filtration chromatography, ion-exchange chromatography, affinity chromatography, electrophoresis, isoelectrofocusing and isoelectric fractionation are suitably used in combination.

The present invention attains the aforesaid object, and encompasses a novel protein possessing a metastasis-inhibitory activity, a DNA coding said protein, and the preparation of said protein.

The following experiments will explain the present invention.

EXPERIMENT 1

Assay for metastasis-inhibitory activity

In accordance with the method of Y. Naomoto et al. described in *Journal of Cancer Research and Clinical Oncology*, Vol.113, pp.544–549 (1987), a metastasis-inhibitory activity was assayed with a model wherein RPMI 4788 cells (FERM BP-2429) are transplanted to nude mice so as to induce lung metastasis.

In a test group, 5 or more BALB/c nude mice were injected through their tail veins with 0.2 ml of phosphate buffer containing a test specimen 3 times in total before the cell transplantation, i.e. at 2 day, 1 day and 3 hours before the cell transplantation. From the next day of the transplantation of $2\times10^6$ RPMI 4788 cells per mouse, the mice were successively injected similarly as above with a test specimen one shot per day over a period of 7 days. In a control group, mice were similarly treated as in the test group except for using phosphate buffer free of the test specimen. On the 21st day after the cell transplantation, nude mice were sacrificed, and the number of metastatic nodules formed on the surfaces of the lungs was macroscopically counted. It was judged that a test specimen had a positive activity when the following requirements were fulfilled: (i) The mean value of numbers of lung metastatic nodules formed in the mice in the control group was 50 or more; (ii) the mean value of those in the test group was lowered to ½ or lower against that in the control group; and (iii) the reduction level in (ii) was evaluated as statistically significant.

EXPERIMENT 2

Preparation of supernatant from culture of HPB-MLT cell stimulated with BCG and LPS A new born hamster was first injected with a serum of anti-hamster thymus prepared from rabbits in usual manner, then subcutaneously transplanted with HPB-MLT cells, and bred for 4 weeks in usual manner. About 20 g weight tumor subcutaneously formed in the hamster was cut into pieces, dispersed, washed with serum-free RPMI 1640 medium, and suspended in a fresh preparation of the same medium to give a concentration of $5\times10^6$ cells/ml. The cell suspension was added with 10 µg/ml BCG and incubated at 37° C. for one day. Thereafter, the resultant cell suspension was added with one µg/ml LPS, incubated for one day, and centrifuged to obtain a supernatant.

EXPERIMENT 3

Purification and physicochemical properties of the present protein

The supernatant in Experiment 2 was concentrated by about 20-fold on "AIL 3013", a membrane module commercialized by Asahi Chemical Ind., Tokyo, Japan, and the concentrate was dialyzed against 25 mM imidazol-HCl buffer (pH 7.4). The resultant solution in a dialytic bag was fed to a column packed with "PBE-94", a product of Pharmacia LKB, Uppsala, Sweden, preequilibrated with 25 mM imidazol-HCl buffer (pH 7.4). The column was fed with "Polybuffer 74 (pH 4.0)", commercialized by Pharmacia LKB, Uppsala, Sweden, to fractionate the supernatant, and the resultant fractions were respectively dialyzed against phosphate-buffered saline (PBS), followed by assaying each fraction for cancer metastasis-inhibitory activity. As a result, it was revealed that the fractions eluted between a pH range of 5.0–6.5 had cancer metastasis-inhibitory activity. The active fractions were pooled, and refractionated on a column packed with "Sephacryl S-200", a product commercialized by Pharmacia LKB Uppsala, Sweden. The resultant fractions were assayed for their cancer metastasis-inhibitory activity to test whether or not that the fractions, eluted with a ratio of (Elution volume)/(Void volume) in the range of 0.5–0.65, might have the activity. The active fractions were pooled and dialyzed against 10 mM potassium phosphate buffer (pH 7.4). The solution in a dialytic bag was fed to a column packed with "DEAE-5PW", a product of Tosoh Corporation, Tokyo, Japan, preequilibrated with 10 mM potassium phosphate buffer (pH 7.4), and eluted with a liner gradient of 10–500 mM potassium phosphate buffer (pH 7.4). In this case, a substance with cancer metastasis-inhibitory activity was eluted in fractions with about 70 mM potassium phosphate. The fractions thus obtained were pooled and dialyzed against 10 mM sodium phosphate buffer (pH 6.8), and fed to a hydroxyapatite column commercialized by Toa Nenryo Kogyo K.K., Tokyo, Japan, preequilibrated with 10 mM sodium phosphate buffer (pH 6.8). In this case, cancer metastasis-inhibitory activity was found in non-adsorbed fractions which were then fed to a column packed with "Mono-P", a product of Pharmacia LKB, Upssala, Sweden, preequilibrated with 25 mM bis-tris-iminodiacetate buffer (pH 7.1), and eluted with "Polybuffer® 74 (pH 4.0)", a product of Pharmacia LKB, Uppsala, Sweden, followed by isolating the present protein with cancer metastasis-inhibitory activity. Thus about 70 µg of the present protein was isolated from 50L of the culture supernatant of HPB-MLT cells stimulated with BCG and LPS. The physicochemical properties of the present protein were studied with the isolated protein.

(1) Molecular weight In accordance with the method of U. K. Laemmli described in *Nature*, Vol.227, pp.680–685 (1970), the protein was subjected to sodium dodecyl sulfate polyacrylamide gel electrophoresis (abbreviated as "SDS-PAGE" hereinafter), and the molecular weight was determined to be 45,000±5,000 based on the relative mobility of the protein against marker proteins.

(2) Isoelectric point The isoelectric point of the protein was estimated to be 5.7±0.5 based on the pHs of eluates on a column chromatography using Mono-P column;

(3) Partial amino acid sequence The protein was subjected to SDS-PAGE, and a band corresponding to the molecular weight of about 45,000 in the resultant gel was isolated by cutting. The resultant gel piece was soaked in 100 mM Tris-HCl buffer (pH 9.0) containing 0.1% sodium dodecyl sulfate (SDS) at 37° C. for one hour, and digested at 37° C. overnight by the addition of 5 μg/ml lysyl endopeptidase, an enzyme specimen commercialized by Wako Pure Chemical Industries, Ltd., Tokyo, Japan. The supernatant obtained from the resultant was fractionated on a reverse-phase chromatography using a column of "C-18", commercialized by VYDAC, Hesperia, USA, equipped with a precolumn of DEAE, followed by recovering peptide fragments which were then analyzed on "470A", an amino acid sequencer commercialized by Applied Biosystems Inc., Foster City, USA. The results were as shown in Chemical formulas 3, 4, 5 and 6.

Chemical formula 3 (SEQ ID no:1)

Asp—Ser—Glu—Gly—Tyr—Ile—Tyr—Ala—Arg—Gly—Ala—Gln—Asp—Met—Lys

Chemical formula 4 (SEQ ID no:2)

Glu—His—Trp—Ser—His—Asp—Pro—Phe—Glu

Chemical formula 5 (SEQ ID no:5)

Glu—Trp—Gln—Arg—Leu—Gln—Ser—Asn—Pro—His—Leu—Lys

Chemical formula 6 (SEQ ID no:6)

Leu—Glu—Gly—Gly—Val—Ala—Tyr—Asn—Val—Ile—Pro (4) Solubility in solvent The protein was soluble in water, physiological saline and phosphate buffer.

(5) Biological activity The protein was tested for cancer metastasis-inhibitory activity with the method in Experiment 1. As a result, the number of metastatic nodules was 314+169 in a control group consisting of 5 nude mice, while that in a test group, wherein 5 nude mice were administered with a solution containing 250 μg/ml of the protein, was 100±43.

These confirmed that the protein exhibited a strong cancer metastasis-inhibitory activity.

(6) Stability The protein was dissolved in phosphate buffer (pH 7.2) and allowed to stand at 100° C. for 30 minutes, followed by determining the residual activity with the method in Experiment 1 to give no activity. Thus, it was revealed that the protein was inactivated under the conditions. While the protein was treated by dissolving it in phosphate buffer (pH 7.2), and allowing the resultant solution to stand at 4° C. for one month, followed by assaying the residual activity similarly as above. As a result, no substantial loss of activity was found, and this revealed that the protein was stable under the conditions.

EXPERIMENT 4

Acute toxicity

By using 7 week-old mice, the present protein was tested for acute toxicity. As a result, the $LD_{50}$ in mice of the protein was 50 mg/kg or higher when intravenously administered to the mice, and this revealed that the toxicity was extremely low.

EXPERIMENT 5

Base sequence coding the present protein

In this experiment, the base sequence of the present protein was determined by conventional method as described by T. Maniatis et al. in *Molecular Cloning, A Laboratory Manual,* 2nd edition, published by Cold Spring Harbor Laboratory Press (1989), New York, USA.

EXPERIMENT 5-1

Construction of cDNA library of HPB-MLT cell

HPB-MLT cells obtained by the method in Experiment 2 were suspended in a serum-free RPMI 1640 medium to give a concentration of $5 \times 10^6$ cells/ml. The cell suspension was added with 10 μg/ml BCG and incubated at 37° C. for one day. The culture thus obtained was added with one μg/ml LPS and incubated for 4.5 hours. The resultant culture was centrifuged to obtain cells which were then solubilized with 4M guanidium isocyanate and homogenized. The resultant homogenate was overlaid on 5.7M cesium chloride, and the mixture was centrifuged at 25,000 rpm for 17 hours to obtain the whole RNAs of the cells. Poly (A)+RNA was purified from the whole RNAs on "Oligotex®-dT30<Super>", a bead for purification of poly (A)+RNA commercialized by Daiichi Pure Chemicals, Tokyo, Japan. The purified poly $(A)^+$ RNA was treated with "cDNA synthesis system plus", a product of Amersham International plc, Buckinghashire, England, to synthesize a cDNA under the direction of the appended manual. The cDNA thus obtained was ligated with a $\lambda$gt10 phage DNA by using "cDNA cloning system $\lambda$gt10", a product of Amersham International plc, Buckinghamshire, England. The resultant recombinant phage DNA was packaged by "Lambda($\lambda$) in vitro packaging kit", a product of Amersham International plc, Buckinghamshire, England, to obtain a cDNA library of HPB-MLT cell.

EXPERIMENT 5-2

Construction of radiolabeled DNA probe

Based on the partial amino acid sequence as shown in Chemical formula 3 in Experiment 3, base sequences estimable from the amino acid sequence of Glu-Gly-Tyr-Ile-Tyr-Ala (SEQ ID NO:7) in Chemical formula 3 were synthesized by a DNA synthesizer commercialized by Applied Biosystems, Inc., Foster City, USA. Ninety-six base sequences consisting of 17 synthesized bases are as shown in Table 1.

TABLE 1

| Probe 1: | GAG | GGG | TAT | ATA | TAT | GC | (SEQ ID no:8) |
|---|---|---|---|---|---|---|---|
| | | A | A | C | T | C | |
| | | | T | | C | | |
| | | | C | | | | |

As for the partial amino acid sequence as shown in Chemical formula 5, complementary chains of base sequences, estimable from Asn-Pro-His-Leu-Lys (SEQ ID NO:9) in the partial amino acid sequence in Chemical formula 5, were synthesized similarly as above. Ninety-six base sequences consisting of 14 synthesized bases are as shown in Table 2. The DNAs thus obtained were radiolabeled with [$\gamma$-$^{32}$p] ATP and T4 polynucleotide kinase.

TABLE 2

| Probe 2: | TTG | AGG | TGG | GGG | TT | (SEQ ID no:10) |
|---|---|---|---|---|---|---|
| | A | A | A | A | | |
| | T | | T | | | |
| | C | | C | | | |
| | TTT | AAG | TGG | GGG | TT | (SEQ ID no:11) |
| | C | A | A | A | | |
| | | | T | | | |
| | | | C | | | |

EXPERIMENT 5-3

Screening with radiolabeled DNA probes

A solution of the recombinant λgt10, a cDNA library of HPB-MLT cell prepared in Experiment 5-1, was mixed with an overnight culture of microorganisms of E. coli strain NM 514 in L-broth, and the mixture was incubated at 37° C. for 15 minutes. The resultant was admixed with a soft agar, and the resultant mixture was overlaid on a hard-agar plate and solidified. The resultant agar plate containing the microorganisms were incubated at 37° C. for 8 hours, cooled and overlaid with "Hybond-N filter", a membrane filter of Amersham International plc, Buckinghamshire, England, to transfer the phage and to fix the phage DNA on the membrane filter. In order to prevent a non-specific bonding of the radiolabeled DNA probes with DNAs except for the objective complementary DNA, the membrane filter was soaked in a solution of a salmon sperm DNA commercialized by Sigma Chemical company, St., Louis, USA, to effect prehybridization, followed by screening positive clones by the southern hybridization with the radiolabeled DNA probes in Experiment 5-2. The results in the first screening test with the probe 1 in Table 1 and the second screening test with the probe 2 in Table 2 revealed that 3 positive clones were present among about 600,000 clones. Phage DNAs isolated from the positive clones were digested with a restriction enzyme EcoRI to remove them from vector DNAs, and the length of the inserted fragments were studied on agarose electrophoresis, followed by analyzing a clone having the longest inserted-fragment of about 1.5 kbp.

EXPERIMENT 5-4

Base sequence of gene coding the present protein

From the positive clones obtained in Experiment 5-3, a phage DNA was isolated and digested with a restriction enzyme EcoRI, and the resultant fragments were separated on SDS-PAGE to obtain an inserted DNA fragment of about 1.5 kbp which was then ligated with a pUC18 plasmid with a ligation kit commercialized by Amersham International plc, Buckinghashire, England, to obtain a recombinant plasmid. The recombinant plasmid thus obtained was introduced in usual manner into E. coli to obtain a recombinant microorganism, and from which a plasmid DNA was prepared. The dideoxy chain termination method was applied to the resultant plasmid DNA to reveal the base sequence of the present protein. Based on the base sequence, the amino acid sequence of the present protein was estimated. As a result, it was revealed that the present DNA consisted of 1,224 bases and coded a protein consisting of 408 amino acids. The estimated amino acid sequence encompassed the amino acid sequences as shown in Chemical formulas 3, 4, 5 and 6 in Experiment 3.

The following is an example of the preparation of the present protein.

EXAMPLE

Similarly as the method in Experiment 2, MOLT-4 cell (ATCC CRL 1582), an established cell line derived from human T-cell leukemia commercialized by Dainippon Pharmaceutical Co., Ltd., Tokyo, Japan, were cultured in a nutrient culture medium while stimulating the cells with BCG and LPS. Similarly as in Experiment 3, a supernatant prepared from the resultant culture was treated to obtain the present protein possessing cancer metastasis-inhibitory activity. The yield was about 40 μg per 50L of the culture supernatant. The protein had the same physicochemical properties as the one in Experiment 3.

The protein according to the present invention effectively inhibits the metastasis of cancers, and this renders it advantageously useful as prophylactic-, therapeutic- and diagnostic-agents for cancer metastases. The toxicity of the present protein is satisfactorily low, because of this it can be systematically administered to patients in the form of an injection, sublingual agent, and the like.

The present protein having the aforesaid advantages is prepared in an industrial scale by the present preparation.

The DNA coding the present protein is useful in the preparation of the present protein by genetic engineering techniques.

While there has been described what is at present considered to be the preferred embodiments of the invention, it will be understood the various modifications may be made therein, and it is intended to cover the appended claims all such modifications as fall within the true spirits and scope of the invention.

---

We claim:

1. A process for preparing protein which comprises:

(a) culturing a cell capable of producing a protein in a nutrient culture medium to form said protein said cell being selected from the group consisting of natural human cells, transformed animal cells, and transformed microorganisms;

(b) purifying said protein by combining at least two techniques from the group consisting of salting out, dialysis, centrifugation, gel filtration, chromatography, ion-exchange chromatography, affinity chromatography, electrophoresis, isoelectric focusing, and isoelectric fractionation to purify said protein, wherein said purified protein has the following physicochemical properties:

(1) Molecular weight 45,000±5,000;

(2) Isoelectric point pI=5.7±0.5;

(3) Partial amino acid sequence Possessing a partial amino acid sequence of Asp-Ser-Glu-Gly-Tyr-Ile-Tyr-Ala-Arg-Gly-Ala-Gln-Asp-Met-Lys-(SEQ ID NO: 1) or Glu-His-Trp-Ser-His-Asp-Pro-Phe-Glu-(SEQ ID NO: 2);

(4) Solubility in solvent Soluble in water, physiological saline and phosphate buffer;

(5) Biological activity Exhibiting metastasis-inhibitory activity on RPMI 4788 cell (FERM BP-2429), an established cell line derived from human colon cancer;

(6) Stability Inactivated in water at pH 7.2 and 100° C. for 30 minutes and being stable in water at pH 7.2 and 4° C. for one month;

(7) Acute toxicity Having an $LD_{50}$ of at least 50 mg/kg mouse on an intravenous administration; and (c) recovering said protein in purified form.

2. The process of claim 1, wherein said protein has an amino acid sequence selected from the group consisting of the amino acid sequence of chemical formula 1: (SEQ ID No: 4):

---
Chemical formula 1

1 Met—Thr—Ser—Lys—Gly—Pro—Glu—Glu—Glu—His—
11 Pro—Ser—Val—Thr—Leu—Phe—Arg—Gln—Tyr—Leu—

---
-continued

Chemical formula 1

21 Arg—Ile—Arg—Thr—Val—Gln—Pro—Lys—Pro—Asp—
31 Tyr—Gly—Ala—Ala—Val—Ala—Phe—Phe—Glu—Glu—
41 Thr—Ala—Arg—Gln—Leu—Gly—Leu—Gly—Cys—Gln—
51 Lys—Val—Glu—Val—Ala—Pro—Gly—Tyr—Val—Val—
61 Thr—Val—Leu—Thr—Trp—Pro—Gly—Thr—Asn—Pro—
71 Thr—Leu—Ser—Ser—Ile—Leu—Leu—Asn—Ser—His—
81 Thr—Asp—Val—Val—Pro—Val—Phe—Lys—Glu—His—
91 Trp—Ser—His—Asp—Pro—Phe—Glu—Ala—Phe—Lys—
101 Asp—Ser—Glu—Gly—Tyr—Ile—Tyr—Ala—Arg—Gly—
111 Ala—Gln—Asp—Met—Lys—Cys—Val—Ser—Ile—Gln—
121 Tyr—Leu—Glu—Ala—Val—Arg—Arg—Leu—Lys—Val—
131 Glu—Gly—His—Arg—Phe—Pro—Arg—Thr—Ile—His—
141 Met—Thr—Phe—Val—Pro—Asp—Glu—Glu—Val—Gly—
151 Gly—His—Gln—Gly—Met—Glu—Leu—Phe—Val—Gln—
161 Arg—Pro—Glu—Phe—His—Ala—Leu—Arg—Ala—Gly—
171 Phe—Ala—Leu—Asp—Glu—Gly—Ile—Ala—Asn—Pro—
181 Thr—Asp—Ala—Phe—Thr—Val—Phe—Tyr—Ser—Glu—
191 Arg—Ser—Pro—Trp—Trp—Val—Arg—Val—Thr—Ser—
201 Thr—Gly—Arg—Pro—Gly—His—Ala—Ser—Arg—Phe—
211 Met—Glu—Asp—Thr—Ala—Ala—Glu—Lys—Leu—His—
221 Lys—Val—Val—Asn—Ser—Ile—Leu—Ala—Phe—Arg—
231 Glu—Lys—Glu—Trp—Gln—Arg—Leu—Gln—Ser—Asn—
241 Pro—His—Leu—Lys—Glu—Gly—Ser—Val—Thr—Ser—
251 Val—Asn—Leu—Thr—Lys—Leu—Glu—Gly—Gly—Val—
261 Ala—Tyr—Asn—Val—Ile—Pro—Ala—Thr—Met—Ser—
271 Ala—Ser—Phe—Asp—Phe—Arg—Val—Ala—Pro—Asp—
281 Val—Asp—Phe—Lys—Ala—Phe—Glu—Glu—Gln—Leu—
291 Gln—Ser—Trp—Cys—Gln—Ala—Ala—Gly—Glu—Gly—
301 Val—Thr—Leu—Glu—Phe—Ala—Gln—Lys—Trp—Met—
311 His—Pro—Gln—Val—Thr—Pro—Thr—Asp—Asp—Ser—
321 Asn—Pro—Trp—Trp—Ala—Ala—Phe—Ser—Arg—Val—
331 Cys—Lys—Asp—Met—Asn—Leu—Thr—Leu—Glu—Pro—
341 Glu—Ile—Met—Pro—Ala—Ala—Thr—Asp—Asn—Arg—
351 Tyr—Ile—Arg—Ala—Val—Gly—Val—Pro—Ala—Leu—
361 Gly—Phe—Ser—Pro—Met—Asn—Arg—Thr—Pro—Val—
371 Leu—Leu—His—Asp—His—Asp—Glu—Arg—Leu—His—
381 Glu—Ala—Val—Phe—Leu—Arg—Gly—Val—Asp—Ile—
391 Tyr—Thr—Arg—Leu—Leu—Pro—Ala—Leu—Ala—Ser—
401 Val—Pro—Ala—Leu—Pro—Ser—Asp—Ser.

---

3. The process of claim 1, wherein said human cell is derived from human T-cell leukemia.

4. The process of claim 3, wherein said human cell derived from human T-cell leukemia is HPB-MLT cell (FERM BP-2430) or MOLT-4 cell (ATCC CRL 1582).

5. The process of claim 1, wherein the step (a) includes contacting said cell with *Bacille Calmette-Guérin* and lysaccharide as an inducer of said protein.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Asp Ser Glu Gly Tyr Ile Tyr Ala Arg Gly Ala Gln Asp Met Lys
1               5                       10                      15

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Glu His Trp Ser His Asp Pro Phe Glu
1               5

( 2 ) INFORMATION FOR SEQ ID NO:3:

( i ) SEQUENCE CHARACTERISTICS:
        ( A ) LENGTH: 1224 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1224

( x i ) SEQUENCE DESCRIPTION: SEQ ID NO:3:

```
ATG ACC AGC AAG GGT CCC GAG GAG GAG CAC CCA TCG GTG ACG CTC TTC        48
Met Thr Ser Lys Gly Pro Glu Glu Glu His Pro Ser Val Thr Leu Phe
 1           5                   10                      15

CGC CAG TAC CTG CGT ATC CGC ACT GTC CAG CCC AAG CCT GAC TAT GGA        96
Arg Gln Tyr Leu Arg Ile Arg Thr Val Gln Pro Lys Pro Asp Tyr Gly
             20                  25                      30

GCT GCT GTG GCT TTC TTT GAG GAG ACA GCC CGC CAG CTG GGC CTG GGC       144
Ala Ala Val Ala Phe Phe Glu Glu Thr Ala Arg Gln Leu Gly Leu Gly
         35                  40                      45

TGT CAG AAA GTA GAG GTG GCA CCT GGC TAT GTG GTG ACC GTG TTG ACC       192
Cys Gln Lys Val Glu Val Ala Pro Gly Tyr Val Val Thr Val Leu Thr
     50                  55                      60

TGG CCA GGC ACC AAC CCT ACA CTC TCC TCC ATC TTG CTC AAC TCC CAC       240
Trp Pro Gly Thr Asn Pro Thr Leu Ser Ser Ile Leu Leu Asn Ser His
 65                  70                      75                  80

ACG GAT GTG GTG CCT GTC TTC AAG GAA CAT TGG AGT CAC GAC CCC TTT       288
Thr Asp Val Val Pro Val Phe Lys Glu His Trp Ser His Asp Pro Phe
                 85                  90                      95

GAG GCC TTC AAG GAT TCT GAG GGC TAC ATC TAT GCC AGG GGT GCC CAG       336
Glu Ala Phe Lys Asp Ser Glu Gly Tyr Ile Tyr Ala Arg Gly Ala Gln
             100                 105                     110

GAC ATG AAG TGC GTC AGC ATC CAG TAC CTG GAA GCT GTG AGG AGG CTG       384
Asp Met Lys Cys Val Ser Ile Gln Tyr Leu Glu Ala Val Arg Arg Leu
         115                 120                     125

AAG GTG GAG GGC CAC CGG TTC CCC AGA ACC ATC CAC ATG ACC TTT GTG       432
Lys Val Glu Gly His Arg Phe Pro Arg Thr Ile His Met Thr Phe Val
     130                 135                     140

CCT GAT GAG GAG GTT GGG GGT CAC CAA GGC ATG GAG CTG TTC GTG CAG       480
Pro Asp Glu Glu Val Gly Gly His Gln Gly Met Glu Leu Phe Val Gln
145                 150                     155                 160

CGG CCT GAG TTC CAC GCC CTG AGG GCA GGC TTT GCC CTG GAT GAG GGC       528
```

```
Arg  Pro  Glu  Phe  His  Ala  Leu  Arg  Ala  Gly  Phe  Ala  Leu  Asp  Glu  Gly
               165                      170                      175

ATA  GCC  AAT  CCC  ACT  GAT  GCC  TTC  ACT  GTC  TTT  TAT  AGT  GAG  CGG  AGT       576
Ile  Ala  Asn  Pro  Thr  Asp  Ala  Phe  Thr  Val  Phe  Tyr  Ser  Glu  Arg  Ser
               180                      185                      190

CCC  TGG  TGG  GTG  CGG  GTT  ACC  AGC  ACT  GGG  AGG  CCA  GGC  CAT  GCC  TCA       624
Pro  Trp  Trp  Val  Arg  Val  Thr  Ser  Thr  Gly  Arg  Pro  Gly  His  Ala  Ser
          195                      200                      205

CGC  TTC  ATG  GAG  GAC  ACA  GCA  GCA  GAG  AAG  CTG  CAC  AAG  GTT  GTA  AAC       672
Arg  Phe  Met  Glu  Asp  Thr  Ala  Ala  Glu  Lys  Leu  His  Lys  Val  Val  Asn
     210                      215                      220

TCC  ATC  CTG  GCA  TTC  CGG  GAG  AAG  GAA  TGG  CAG  AGG  CTG  CAG  TCA  AAC       720
Ser  Ile  Leu  Ala  Phe  Arg  Glu  Lys  Glu  Trp  Gln  Arg  Leu  Gln  Ser  Asn
225                 230                      235                      240

CCC  CAC  CTG  AAA  GAG  GGG  TCC  GTG  ACC  TCC  GTG  AAC  CTG  ACT  AAG  CTA       768
Pro  His  Leu  Lys  Glu  Gly  Ser  Val  Thr  Ser  Val  Asn  Leu  Thr  Lys  Leu
                    245                      250                      255

GAG  GGT  GGC  GTG  GCC  TAT  AAC  GTG  ATA  CCT  GCC  ACC  ATG  AGC  GCC  AGC       816
Glu  Gly  Gly  Val  Ala  Tyr  Asn  Val  Ile  Pro  Ala  Thr  Met  Ser  Ala  Ser
               260                      265                      270

TTT  GAC  TTC  CGT  GTG  GCA  CCG  GAT  GTG  GAC  TTC  AAG  GCT  TTT  GAG  GAG       864
Phe  Asp  Phe  Arg  Val  Ala  Pro  Asp  Val  Asp  Phe  Lys  Ala  Phe  Glu  Glu
          275                      280                      285

CAG  CTG  CAG  AGC  TGG  TGC  CAG  GCA  GCT  GGC  GAG  GGG  GTC  ACC  CTA  GAG       912
Gln  Leu  Gln  Ser  Trp  Cys  Gln  Ala  Ala  Gly  Glu  Gly  Val  Thr  Leu  Glu
     290                      295                      300

TTT  GCT  CAG  AAG  TGG  ATG  CAC  CCC  CAA  GTG  ACA  CCT  ACT  GAT  GAC  TCA       960
Phe  Ala  Gln  Lys  Trp  Met  His  Pro  Gln  Val  Thr  Pro  Thr  Asp  Asp  Ser
305                      310                      315                      320

AAC  CCT  TGG  TGG  GCA  GCT  TTT  AGC  CGG  GTC  TGC  AAG  GAT  ATG  AAC  CTC      1008
Asn  Pro  Trp  Trp  Ala  Ala  Phe  Ser  Arg  Val  Cys  Lys  Asp  Met  Asn  Leu
                    325                      330                      335

ACT  CTG  GAG  CCT  GAG  ATC  ATG  CCT  GCT  GCC  ACT  GAC  AAC  CGC  TAT  ATC      1056
Thr  Leu  Glu  Pro  Glu  Ile  Met  Pro  Ala  Ala  Thr  Asp  Asn  Arg  Tyr  Ile
               340                      345                      350

CGC  GCG  GTG  GGG  GTC  CCA  GCT  CTA  GGC  TTC  TCA  CCC  ATG  AAC  CGC  ACA      1104
Arg  Ala  Val  Gly  Val  Pro  Ala  Leu  Gly  Phe  Ser  Pro  Met  Asn  Arg  Thr
          355                      360                      365

CCT  GTG  CTG  CTG  CAC  GAC  CAC  GAT  GAA  CGG  CTG  CAT  GAG  GCT  GTG  TTC      1152
Pro  Val  Leu  Leu  His  Asp  His  Asp  Glu  Arg  Leu  His  Glu  Ala  Val  Phe
     370                      375                      380

CTC  CGT  GGG  GTG  GAC  ATA  TAT  ACA  CGC  CTG  CTG  CCT  GCC  CTT  GCC  AGT      1200
Leu  Arg  Gly  Val  Asp  Ile  Tyr  Thr  Arg  Leu  Leu  Pro  Ala  Leu  Ala  Ser
385                      390                      395                      400

GTG  CCT  GCC  CTG  CCC  AGT  GAC  AGC                                              1224
Val  Pro  Ala  Leu  Pro  Ser  Asp  Ser
                    405
```

( 2 ) INFORMATION FOR SEQ ID NO:4:

( i ) SEQUENCE CHARACTERISTICS:
        ( A ) LENGTH: 408 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Thr  Ser  Lys  Gly  Pro  Glu  Glu  Glu  His  Pro  Ser  Val  Thr  Leu  Phe
  1                 5                        10                       15

Arg  Gln  Tyr  Leu  Arg  Ile  Arg  Thr  Val  Gln  Pro  Lys  Pro  Asp  Tyr  Gly
               20                       25                       30
```

```
Ala  Ala  Val  Ala  Phe  Phe  Glu  Glu  Thr  Ala  Arg  Gln  Leu  Gly  Leu  Gly
          35                       40                      45

Cys  Gln  Lys  Val  Glu  Val  Ala  Pro  Gly  Tyr  Val  Val  Thr  Val  Leu  Thr
          50                       55                      60

Trp  Pro  Gly  Thr  Asn  Pro  Thr  Leu  Ser  Ser  Ile  Leu  Leu  Asn  Ser  His
65                       70                      75                           80

Thr  Asp  Val  Val  Pro  Val  Phe  Lys  Glu  His  Trp  Ser  His  Asp  Pro  Phe
                    85                       90                           95

Glu  Ala  Phe  Lys  Asp  Ser  Glu  Gly  Tyr  Ile  Tyr  Ala  Arg  Gly  Ala  Gln
               100                      105                     110

Asp  Met  Lys  Cys  Val  Ser  Ile  Gln  Tyr  Leu  Glu  Ala  Val  Arg  Arg  Leu
               115                      120                     125

Lys  Val  Glu  Gly  His  Arg  Phe  Pro  Arg  Thr  Ile  His  Met  Thr  Phe  Val
          130                      135                     140

Pro  Asp  Glu  Glu  Val  Gly  Gly  His  Gln  Gly  Met  Glu  Leu  Phe  Val  Gln
145                      150                     155                          160

Arg  Pro  Glu  Phe  His  Ala  Leu  Arg  Ala  Gly  Phe  Ala  Leu  Asp  Glu  Gly
                    165                     170                     175

Ile  Ala  Asn  Pro  Thr  Asp  Ala  Phe  Thr  Val  Phe  Tyr  Ser  Glu  Arg  Ser
               180                      185                     190

Pro  Trp  Trp  Val  Arg  Val  Thr  Ser  Thr  Gly  Arg  Pro  Gly  His  Ala  Ser
          195                      200                     205

Arg  Phe  Met  Glu  Asp  Thr  Ala  Ala  Glu  Lys  Leu  His  Lys  Val  Val  Asn
     210                      215                     220

Ser  Ile  Leu  Ala  Phe  Arg  Glu  Lys  Glu  Trp  Gln  Arg  Leu  Gln  Ser  Asn
225                      230                     235                          240

Pro  His  Leu  Lys  Glu  Gly  Ser  Val  Thr  Ser  Val  Asn  Leu  Thr  Lys  Leu
               245                      250                     255

Glu  Gly  Gly  Val  Ala  Tyr  Asn  Val  Ile  Pro  Ala  Thr  Met  Ser  Ala  Ser
               260                      265                     270

Phe  Asp  Phe  Arg  Val  Ala  Pro  Asp  Val  Asp  Phe  Lys  Ala  Phe  Glu  Glu
          275                      280                     285

Gln  Leu  Gln  Ser  Trp  Cys  Gln  Ala  Ala  Gly  Glu  Gly  Val  Thr  Leu  Glu
     290                      295                     300

Phe  Ala  Gln  Lys  Trp  Met  His  Pro  Gln  Val  Thr  Pro  Thr  Asp  Asp  Ser
305                      310                     315                          320

Asn  Pro  Trp  Trp  Ala  Ala  Phe  Ser  Arg  Val  Cys  Lys  Asp  Met  Asn  Leu
               325                      330                     335

Thr  Leu  Glu  Pro  Glu  Ile  Met  Pro  Ala  Ala  Thr  Asp  Asn  Arg  Tyr  Ile
               340                      345                     350

Arg  Ala  Val  Gly  Val  Pro  Ala  Leu  Gly  Phe  Ser  Pro  Met  Asn  Arg  Thr
          355                      360                     365

Pro  Val  Leu  Leu  His  Asp  His  Asp  Glu  Arg  Leu  His  Glu  Ala  Val  Phe
     370                      375                     380

Leu  Arg  Gly  Val  Asp  Ile  Tyr  Thr  Arg  Leu  Leu  Pro  Ala  Leu  Ala  Ser
385                      390                     395                          400

Val  Pro  Ala  Leu  Pro  Ser  Asp  Ser
               405
```

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:5:

Glu Trp Gln Arg Leu Gln Ser Asn Pro His Leu Lys
1               5                   10

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Leu Glu Gly Gly Val Ala Tyr Asn Val Ile Pro
1               5                   10

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Glu Gly Tyr Ile Tyr Ala
1               5

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GAGGGGTATA TATATGC                                                                              17

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Asn Pro His Leu Lys
1               5

(2) INFORMATION FOR SEQ ID NO:10:

(i) SEQUENCE CHARACTERISTICS:
        (A) LENGTH: 14 base pairs
        (B) TYPE: nucleic acid
        (C) STRANDEDNESS: single
        (D) TOPOLOGY: linear ( i i ) MOLECULE TYPE: cDNA ( x i ) SEQUENCE DESCRIPTION: SEQ ID NO:10:

TTGAGGTGGG GGTT 14

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TTTAAGTGGG GGTT 14